United States Patent [19]

Wilson

[11] Patent Number: 5,123,056
[45] Date of Patent: Jun. 16, 1992

[54] WHOLE-LEG X-RAY IMAGE PROCESSING AND DISPLAY TECHNIQUES

[75] Inventor: David L. Wilson, Trenton, N.J.

[73] Assignee: Siemens Medical Systems, Inc., Iselin, N.J.

[21] Appl. No.: 474,420

[22] Filed: Feb. 2, 1990

[51] Int. Cl.⁵ .............................................. G06K 9/00
[52] U.S. Cl. .................................... 382/6; 382/1; 364/413.73; 358/111
[58] Field of Search ............. 382/6, 19, 1, 54, 8; 364/413.13, 413.17, 413.15, 413.23, 413.22; 358/111, 167, 166, 169

[56] References Cited

U.S. PATENT DOCUMENTS

| 4,339,799 | 7/1982 | Abele et al. | 382/6 |
| 4,495,645 | 1/1985 | Ohhashi | 382/6 |
| 4,609,940 | 9/1986 | Born et al. | 358/111 |
| 4,613,983 | 9/1986 | Yedid et al. | 378/99 |
| 4,633,494 | 12/1986 | Klausz | 378/205 |
| 4,792,900 | 12/1988 | Sones et al. | 382/6 |
| 4,802,093 | 1/1989 | Ema | 382/6 |
| 4,862,358 | 8/1989 | Kimura et al. | 382/6 |
| 4,907,156 | 3/1990 | Doi et al. | 382/6 |
| 4,920,491 | 4/1990 | Eberhard et al. | 382/6 |

Primary Examiner—Michael Razavi
Attorney, Agent, or Firm—Lawrence C. Edelman

[57] ABSTRACT

An X-ray examination device having an imaging area which is less than the length of an object to be imaged, acquires a series of high-resolution input images at selected different positions which overlap along the length of the object. The high-resolution images are processed in accordance with first and second methods for later application to a display device. The first method creates a low-resolution composite image for display which is simutaneously representative of a plurality of the high-resolution acquired images, and the second method determines portions of each of the acquired images which are to be deleted and provides to the display the series of high-resolution images in a scroll fashion with the predetermined portions deleted from the adjacent images. The user has control means for controllably indicating a position (region of interest) on the display for causing the display to provide a high-resolution image which is centered about the region of interest. Additionally, the control means provides control signals to a gantry control apparatus for centering the X-ray examination device over the region of interest. Finally, a processing method and apparatus is provided for displaying the scrolled images in a visually pleasing manner wherein the portions of adjacent images to be deleted is determined by providing continuity for identifiable features of the high-resolution images.

10 Claims, 6 Drawing Sheets

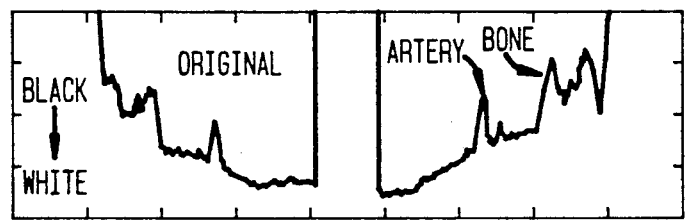
*FIG. 4A*
INTENSITY
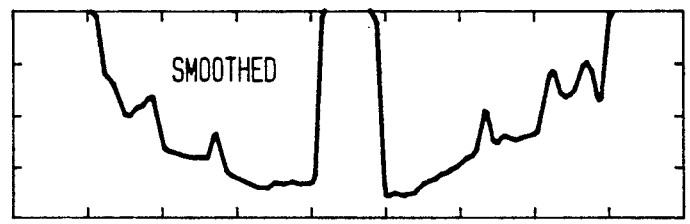
*FIG. 4B*
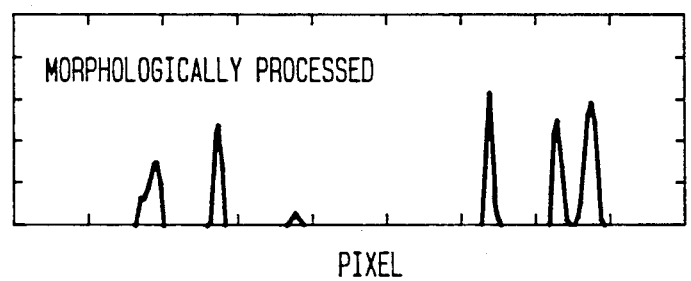
*FIG. 4C*
PIXEL
*FIG. 5*
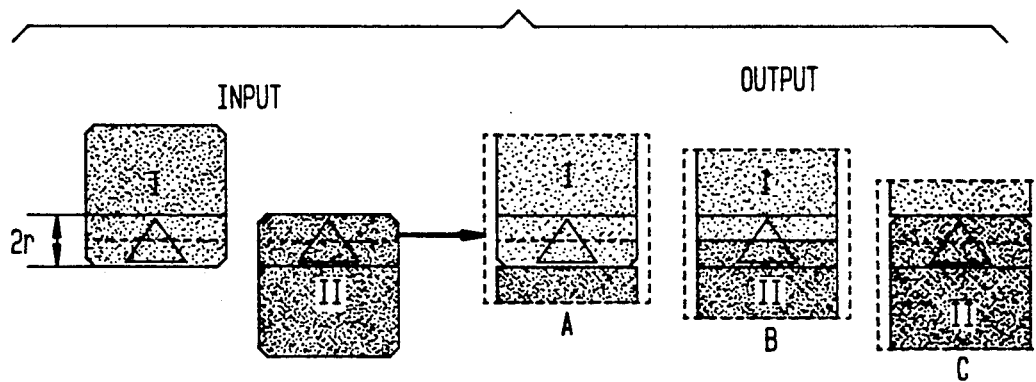

WHOLE-LEG X-RAY IMAGE PROCESSING AND DISPLAY TECHNIQUES

BACKGROUND OF THE INVENTION

1. Field of the Invention

The invention relates to an X-ray examination/diagnostic apparatus including an X-ray source and an X-ray image detection device which are mutually displacable with respect to an object to be examined, and more particularly, to a method and apparatus for processing and displaying an image of the object, wherein the object is larger than the imaging field of the X-ray image detection device. The invention finds a preferred field of application in angiography, in particular for visualizing at least a large proportion of a patient's blood vessels and circulatory system.

2. Description of the Prior Art

In angiography, it is extremely useful to be able to display as a continuous image a large part of the arterial and/or venous system such as, in particular, the entire lower arterial and venous system. In the past, examinations of this type have been performed by means of an installation comprising an X-ray source placed at a considerable height above the patient in order to irradiate the entire region to be visualized as well as a film transfer mechanism for taking a series of adjacent photographs corresponding to different portions of this region. This system suffers from the double disadvantage of high operating costs arising from the considerable lengths of photographic film used and also arising from extensive irradiation of the patient. Furthermore, it is not always easy to read the document by reason of the variations in quality of the successive images. Additionally, such large films are difficult to handle. More recently, with the appearance of image intensifiers which tend to replace films, it has been proposed to take a number of digital acquisitions in respect of different relative positions between the source-detector assembly and the patient-supporting table and to reproduce these digital images in a non-continuous manner on a single photographic document of distinctly smaller size than the series of photographs described above for an equivalent resolution of the image. Furthermore, the X-radiation dose applied to the patient is reduced to an appreciable extent. However, this type of presentation calls for an effort of mental reconstruction of the image on the part of the physician, which is considered as a restrictive condition.

Presently, digital X-ray examination apparatus for vascular imaging are now widely used and well known in the literature, e.g., from U.S. Pat. No. 4,204,225 entitled REAL TIME DIGITAL X-RAY SUBTRACTION IMAGING. In such a device for digital subtraction imaging, X-ray images of a portion of a patient are recorded both before a contrast medium is injected into the patient as well as after injection of the contrast medium into the patient. Both sets of images are stored and digitized and then processed so that the images without the contrast medium (referred to hereinafter as mask images) are subtracted from the contrast-filled images (referred to hereinafter as contrast images) with a result that the contrast-filled vascular system becomes highly visible upon display of the processed images. During examination of, for example, parts of the body of the patient which do not fit within a single image field of the X-ray image detection device, the images are acquired from a plurality of different locations along the length of the patient. Programmable stepping tables or gantrys provide the required relative movement between the X-ray examination device and the patient.

It is an object of the invention to facilitate X-ray examinations and diagnosis for larger parts of the body larger than the optical input of the X-ray image detection device, by appropriate processing and display of a series of X-ray images acquired along the length of the body.

SUMMARY OF THE INVENTION

An X-ray examination device having an imaging area which is less than the length of an object to be imaged, acquires a series of high-resolution input images at selected different positions which overlap along the length of the object. The high-resolution images are processed in accordance with first and second methods for later application to a display device. In both methods a determination of portions of each of the acquired images which are to be deleted is made in order to properly join the overlapped images. The first method creates a low-resolution composite image for display which is simultaneously representative of a plurality of the high-resolution acquired images, and the second method provides to the display the series of high-resolution images in a scroll fashion with the deletion of the portions of the images being apportioned between.

The user has control means for indicating a position (region of interest) on the display for causing the display to provide a high-resolution image which is centered about the region of interest. Additionally, the control means provides control signals to a gantry control apparatus for centering the X-ray examination device over the region of interest. Finally, a processing method and apparatus is provided for displaying the scrolled images in a visually pleasing manner wherein the portions of adjacent images to be deleted is determined by providing continuity for identifiable features of the high-resolution images.

In the preferred embodiment, two methods of image processing are provided in which the best 5-7 images of the peripheral arteries of a patient are joined together to form a single, continuous image of the legs. Firstly, a complete image of both legs, called WHOLE-LEG, is reduced so that it can be displayed on a single monitor or made into hardcopy image. Secondly, adjacent full-resolution images are processed so that they can be scrolled on a display console (SCROLL).

In either method, from the geometrical parameters of the image acquisition system (source-to-detector distance, table height, etc.), the portions of each image to be removed before joining the remaining portions together are estimated. This estimate is refined using an automatic search for the best match. To correct for body taper, images are intensity equalized. It is noted, however, that using a reconstruction method that assumes a planar geometry results in a volume that is displayed in neighboring image frames (i.e., displayed twice) and a volume that is never displayed. Nevertheless, the WHOLE-LEG display is aesthetically pleasing. In the case of SCROLL, the images are displayed in a manner such that every part of each input image is displayed at one time or another.

Other features and advantages of the invention will be apparent from the description of the preferred embodiment and from the claims.

For a fuller understanding of the present invention, reference should now be made to the following detailed description of the preferred embodiment of the invention and to the accompanying drawings.

BRIEF DESCRIPTION OF THE DRAWINGS

FIG. 4a, b, c illustrates a preprocessing method using a morphological filter operation leaves only those peaks which correspond to the major structures in the image (bone edges and arteries) which is used for determining how to join adjacent images together; and FIG. 5 illustrates a method for joining images which is particularly useful for a SCROLL display;

DETAILED DESCRIPTION OF THE PREFERRED EMBODIMENT

Figure 1:
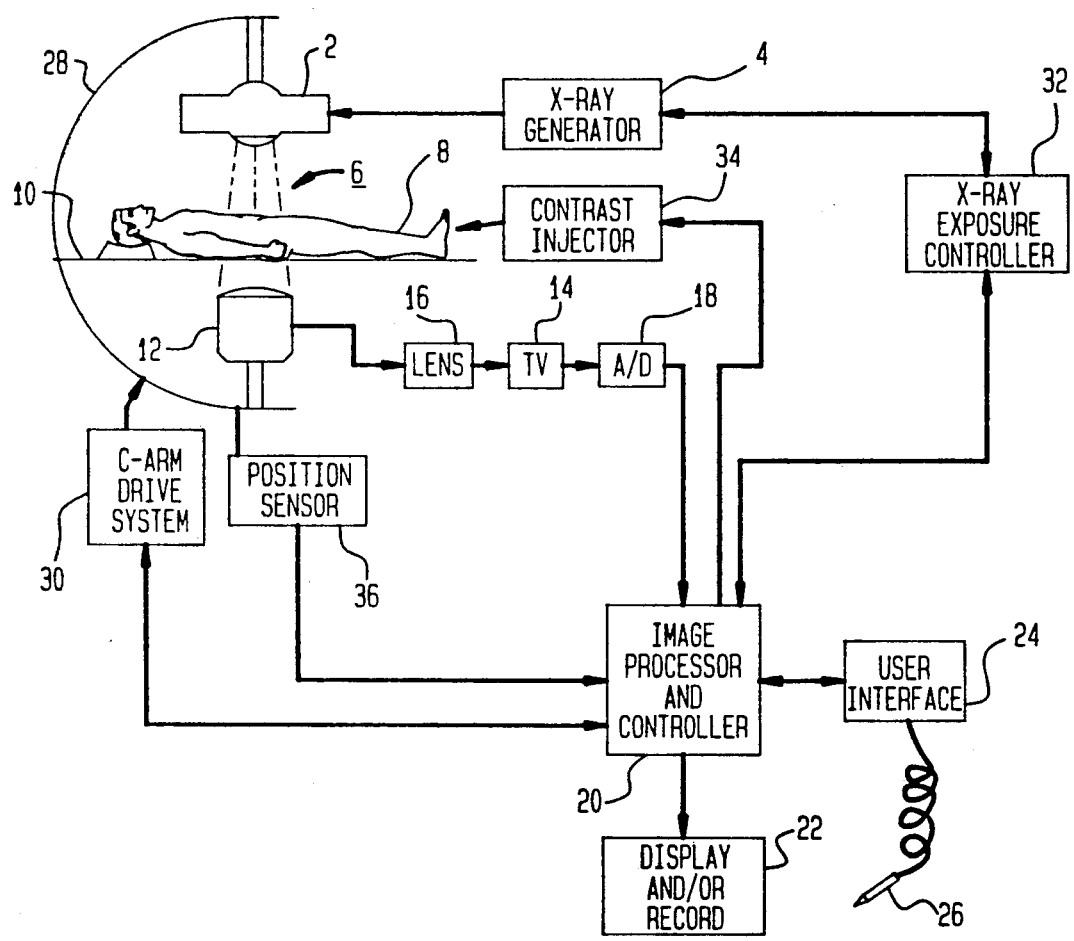
FIG. 1 illustrates in block diagram form an X-ray examination/diagnostic system which processes and displays images in accordance with the present invention.

The X-ray examination apparatus shown in FIG. 1 comprises an X-ray tube 2 which is supplied by an X-ray power generator 4 for generating an X-ray beam 6. A patient 8 is supported on an X-ray table 10 at a position so that the generated X-rays 6 pass through patient 10 and onto an X-ray image intensifier tube 12 located on a side of the patient supporting table 10 which is remote from X-ray tube 2. As well known, the image intensifier tube 12 provides an optical output which is imaged into a television camera 14 by means of a lens system 16. Although the optical output from image intensifier tube 12 would normally be along an axis parallel to the axis of the X-ray beam input, a perpendicular path for the optical output is illustrated solely for the convenience of aiding drawing clarity. The image projected into television camera 14 is converted therein into a video signal. The video signal supplied from camera 14 is then digitized by an analog to digital (A/D) converter 18 and subsequently processed and stored in an image processor and controller 20. A display/record device 22 is used to display and/or record the stored images as, e.g., the result of a digital subtraction examination. A user interface 24 allows a user/operator to control the operation of the X-ray system, as well known. An indicating device, such as a light pen 26 allows the user to identify regions of interest (ROI's) on the display, as also known.

For completing the conventional aspects of the system, a known type of C-arm gantry arrangement 28 is provided to move X-ray tube 2 and image intensifier tube 12 in a coordinated manner with respect to the patient support table 10. For this purpose, a high resolution C-arm drive system 30 is provided, as well as an X-ray exposure controller 32. Also a contrast medium injector 34.

That portion of the X-ray examination apparatus including X-ray tube 2, image intensifier tube 12, television camera 14, C-arm gantry 28, patient supporting table 10, C-arm drive system 30, image processor and controller 20, interface 24 and display 22 are all conventional components well known in the art and may comprise, for example, the ANGIOSKOP D33 gantry system and the DIGITRON 3 X-ray image processing and control system, both available from Siemens Medical Systems, Inc., Iselin, N.J. However, the image processor and controller 20 is modified to operate in accordance with the invention, as described herein. Furthermore, the X-ray power generator 4 and X-ray exposure controller 32 are also known and commercially available components, available from, for example, the forenoted Siemens Medical Systems, Inc. under the respective device tradenames of POLYDOROS 100 and DIGIMATIC. In a preferred embodiment, image processor and controller 20 includes the 1024-by-1024 matrix upgrade for improved image resolution. Contrast injector 29 may comprise a product available from Medrad Corporation under the trademark MARK V. A final component of the system is a position measuring device 36 for accurately indicating the relative position between C-arm 28 and the patient support table 10. For this purpose, a position measuring device 36 comprises, e.g., a component commercially available from Sony Corporation under their trademark DIGIRULER.

Two display types are generated. First, a whole-leg image is reduced so that it fits on a single display or hardcopy image. The result is referred to as WHOLE-LEG. WHOLE-LEG may be useful for physician reports to referring physicians, but is probably not useful for diagnosis. Second, a full-resolution image is assembled so that it can be scrolled on a display console, and it is referred to as SCROLL. SCROLL lets the user both concentrate on a problem area that extends over more than one image frame and allows quick association of the image with anatomy. Very often radiologists show images to referring physicians on a video screen. SCROLL provides a fast, convenient way to review the pertinent images.

WHOLE-LEG and SCROLL are also useful for controlling the gantry: the operator can point to a region of interest on display 22 using light pen 26, which pointing would cause controller 22 to generate the appropriate signals to command C-arm 8 to center X-ray source 2 at that position. Such systems are known in general, see for example U.S. Pat. No. 4,609,940, incorporated herein by reference. Furthermore, the association and storage of the position information corresponding to each acquired image is also known, e.g., from U.S. Pat. No. 4,613,983, which is also incorporated herein by reference.

Additionally, WHOLE-LEG might be useful for controlling a full-resolution image display. That is, when the operator points at a region of interest, those full-resolution images taken at that position could be called up from the memory (not shown) of controller 20 and displayed.

1. Reconstruction Method

Figure 2:
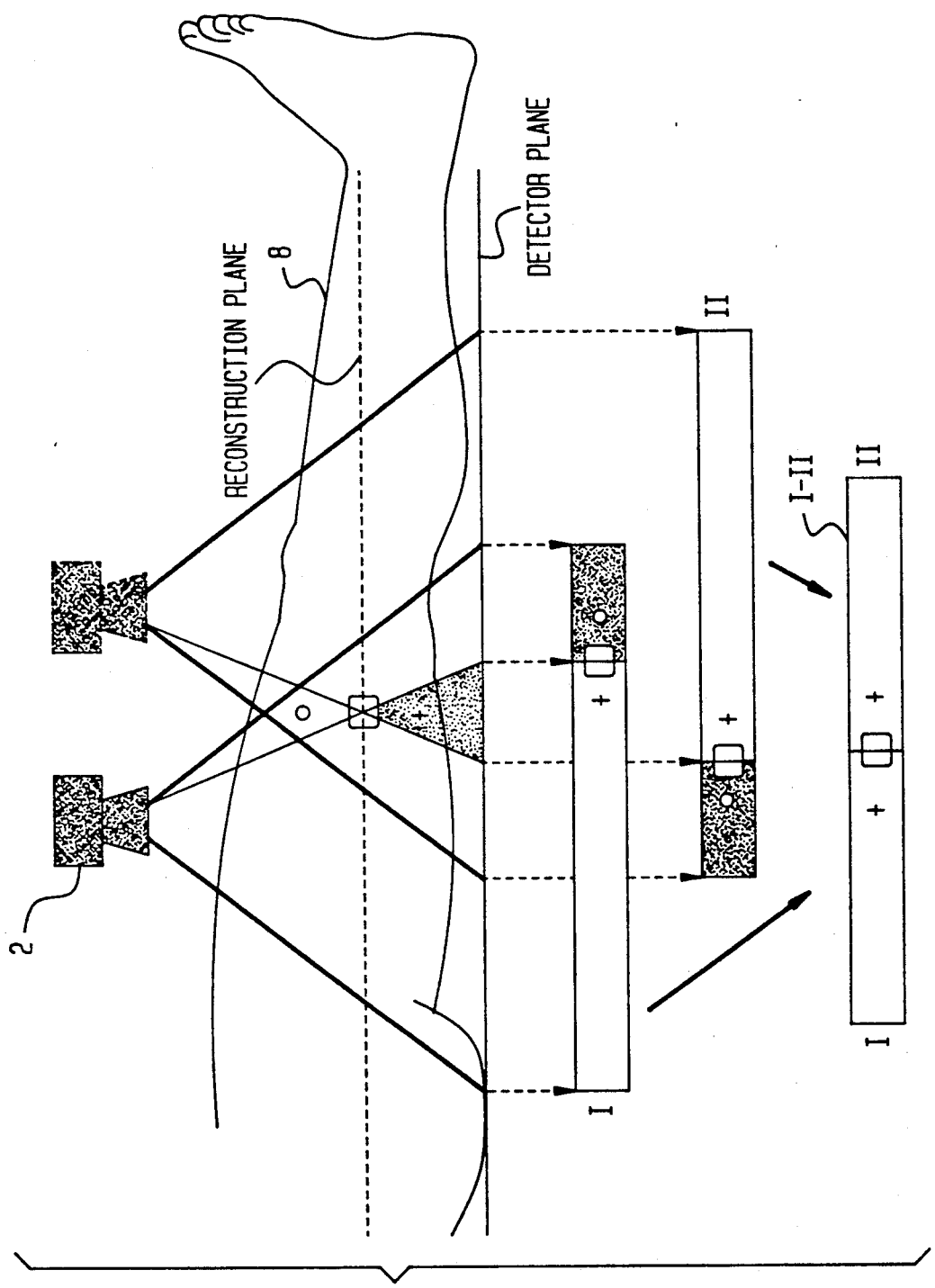
FIG. 2 illustrates the joining together of adjacent images so as to exactly reproduce the reconstruction plane.

In all cases, images are joined together such that a single plane parallel to the image intensifier, hereafter called the reconstruction plane, is reproduced exactly. In FIG. 2 images are acquired with gantry 28 in two successive positions giving rise to adjoining overlapping images I and II. Images I and II shown in FIG. 2 are representative of an "end" or "side" view of the image, i.e., in a digital system, each of images I and II is actually a series of adjacent end pixels in a two dimensional array of pixels, such as a 1024×1024 array. By removing the proper number of pixel rows from each image and joining the results together, a display image (I-II) is formed that exactly reproduces a planar object in the reconstruction plane. However, this leaves a volume above the reconstruction plane which is never displayed (identified by the o) and a volume below (identified by the +) which is displayed twice.

Figure 3:
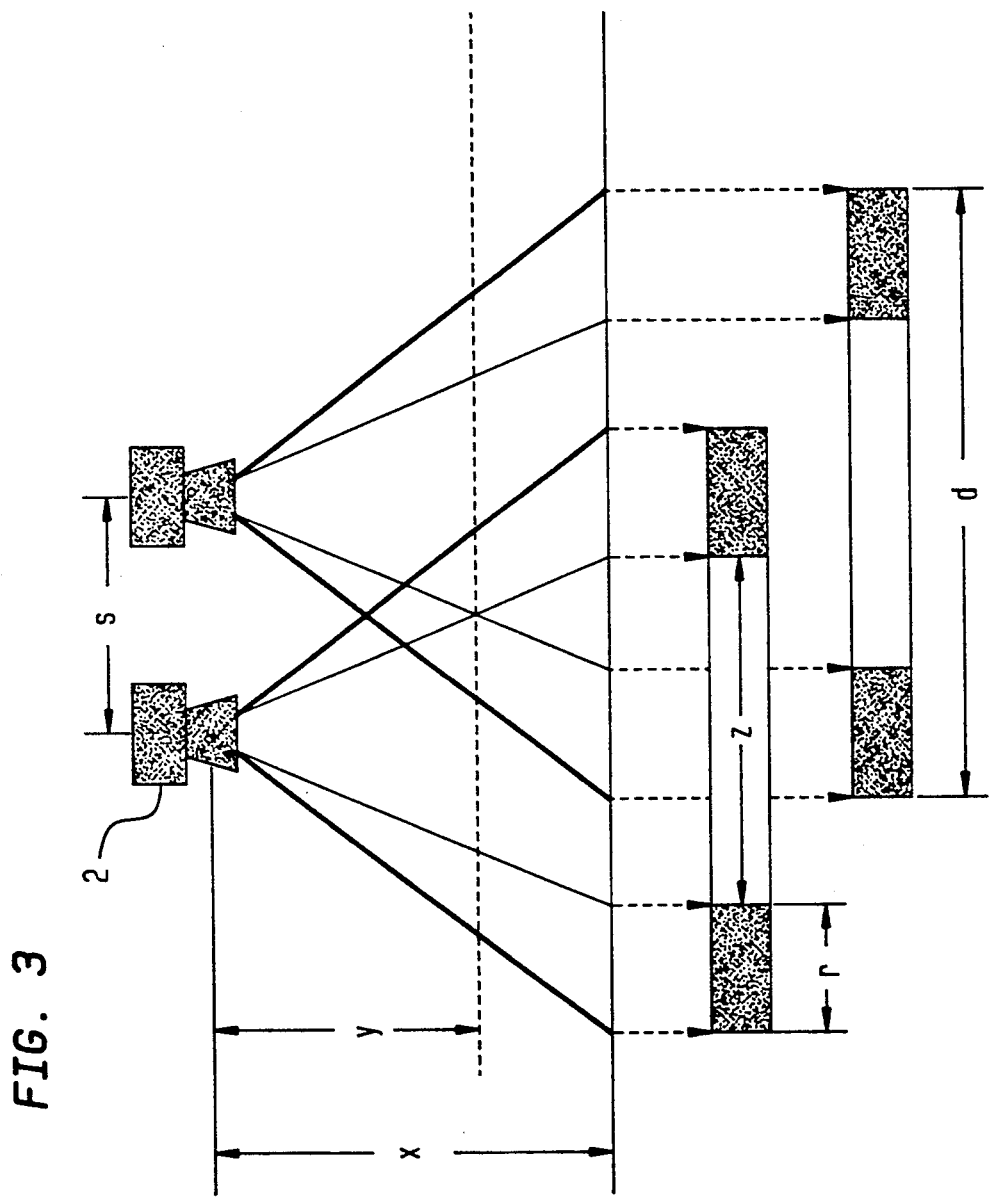
FIG. 3 illustrates the parameters used to develop the theory for joining the images together in accordance with the invention.
Figure 6:
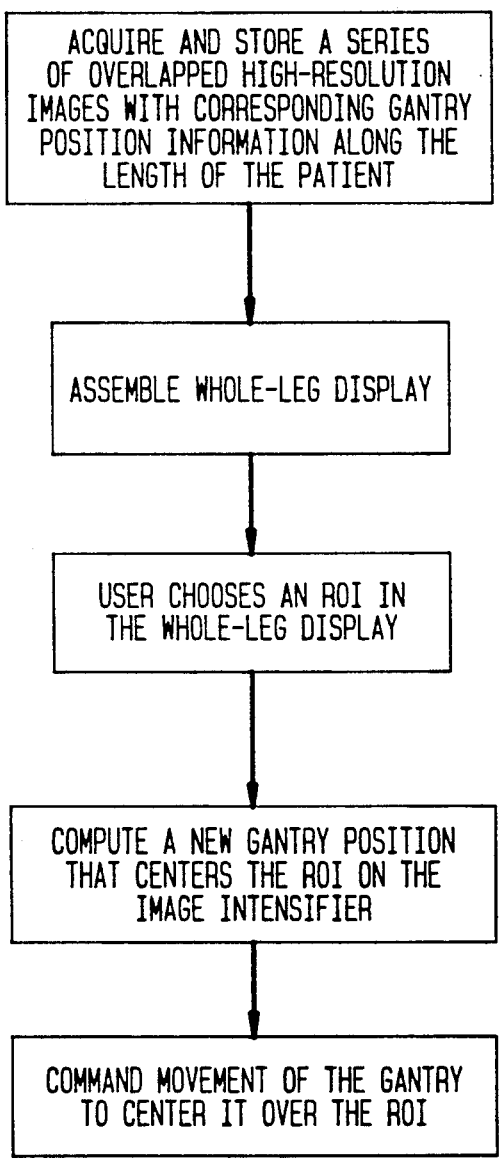
FIG. 6 illustrates gantry control for the WHOLE-LEG display.
Figure 7:
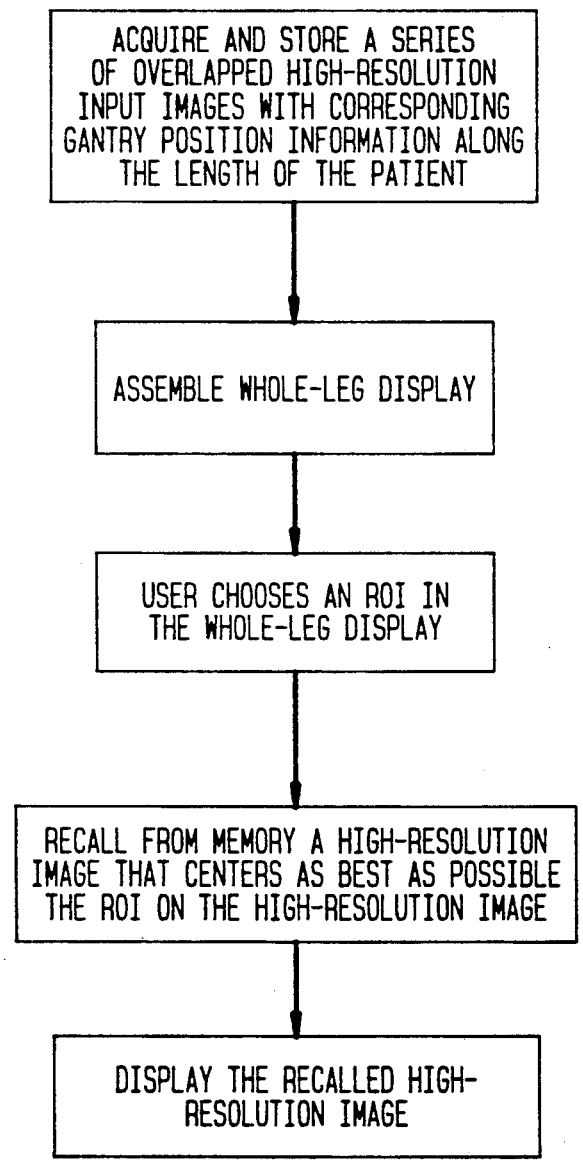
FIG. 7 illustrates high-resolution image display from the WHOLE-LEG display.

In FIG. 3 various geometric parameters are defined that allow one to derive the number of pixel rows to be removed for the reconstruction. The step distance between the two images is s. The source-to-detector distance is x and the source-to-reconstruction plane is y. In the figure, an equal number of pixel rows, identified by the length r, is removed from the end of each image. The distance z is given by $$z = \frac{x}{y} s. \qquad (1)$$

This result is easily obtained by tracing the length s along lines parallel to the reconstruction plane. This length s is then simply magnified by the point source magnification factor x/y, to give z, the length of the image that is not removed in the reconstruction. Except for images acquired at the ends of the patient, pixel rows are removed from both ends of the images to be joined. Thus, using $$2 = r + z = d. \qquad (2)$$

it follows that $$r = \frac{d}{2} - \frac{xs}{2y} \qquad (3)$$

In the SCROLL reconstruction, it is desirable, as described later on, that sometimes unequal portions of adjoining images are removed. In this case, the total number of pixels to be removed for the reconstruction of a given plane is 2 r apportioned in any way between the two images.

Since patients are not flat, using Equation 3, the change in r, r, is obtained for a change in the reconstruction plane, y.

$$r = \frac{xs}{2} \left( \frac{1}{y} - \frac{1}{y + y} \right) \qquad (4)$$

Assuming x = 100 cm, s = 17 cm, y = 77 cm, d = 36 cm, and 1 pixel = 0.4 mm, it is found that r is 7, 17 and 32 pixels for y equal to 3, 5, and 10 cm, respectively.

From the above calculations and from experience in joining leg images, it is clear that the location of the reconstruction plane of interest can not be predetermined with sufficient precision using the geometric parameters of the acquisition. In particular, it is impossible to locate precisely the height of interest above the table top. Thus, in accordance with the present invention, to make a good reconstruction, it is required to search for the number of pixel rows to remove. An automatic method for doing this is described in the next section.

The foregoing calculations indicate that the assumption of a single reconstruction plane is not very good. Nevertheless, it will be seen that there are several reasons that an aesthetically pleasing display can in fact be obtained.

2. Computer Algorithms

2.1 Estimation of adjoining pixel rows

In accordance with an aspect of the invention, an automatic method is used to obtain the number of pixel rows to be removed from the ends of the overlapped adjacent images by searching for the best matching pixel rows from the adjoining images. The objective is to find corresponding pixel rows in each image that give an aesthetically pleasing match to the viewer when they are adjacent to each other. This occurs when the principle structures in the image (bone edges and arteries) are joined continuously. In the preferred embodiment, a similarity measure between candidate pixel rows from adjacent images, $R_1(i)$ and $R_2(i)$, is computed in the image processor consisting of the sum of $|R_1(i) - R_2(i)|$ over all pixels in the rows. Minimizing this measure gives good matching rows.

Before calculating the similarity measure,, the candidate pixel rows are preprocessed in the image processor to emphasize the arteries and bone edges, such as shown in FIG. 4. FIG. 4 illustrates processing for a single row of each image r. FIG. 4a shows the unprocessed or ORIGINAL signal. First, the pixel rows are smoothed using a low-pass filter, as shown in FIG. 4b. Second, to eliminate the background images and to retain only arteries and bone edges, the image signals are morphologically filtered, as shown in FIG. 4c. The morphological filter consists of doing an opening operation using a flat structuring element to create an opened mask that estimates the background. The opened mask is subtracted from the original pixel row to leave just arteries and bone edges. For example, in FIG. 4c, only peaks corresponding to bone edges and arteries remain. Note that outside of these peaks the trace is zero. Thus, following preprocessing only those features needing to be made continuous in the reconstructed image remain.

Opening can be thought of in three dimensions as taking an object e.g., a ball, whose top surface is described by FIG. 4b, pressing it up against the underside intensity surface of the image, i.e., FIG. 4b waveform, and tracing the highest point reached by the object at each pixel in the image to create a mask. In the case where the structuring element is a ball, sharp peaks in the image are eliminated following the opening while wider peaks into which the ball can fit are preserved. Subtraction of this mask from the image results in an enhanced image, FIG. 4c, in which the sharp peaks are retained. Further details relating to Morphological Filtering are known from, e.g., the article entitled "Grayscale morphology" by S. R. Sternberg, Computer Vision, Graphics, and Image Processing, vol. 35, pp. 333-355, 1986, incorporated herein by reference.

A particular problem is that adjoining images can have different collimator settings and certain features may be obscured. Following preprocessing, this can give rise to peaks in one pixel row that are not present in the other pixel row of the candidate pair (e.g., the bone on the left in FIG. 4). A solution in the similarity measure computation is to skip those pixel locations, i, where at least one pixel from either row is zero.

The search for the best matching pixel row pair for adjacent images proceeds as follows. When the leg images are upright, the bottom pixel row of image I is compared with the top pixel row of lower image II.

Subsequent candidate pairs are obtained by moving up and down one pixel row in images I and II, respectively. Implicitly, this search assumes that equal portions of each image are to be removed. After the similarity measure of all candidate pairs has been calculated, the minimum identifies which rows are the best match. Then, the images are joined at that row, r, and the remaining rows in the end portions are discarded.

2.2 Scrolling-whole leg image (SCROLL)

As described in Section 2, joining the images results in a volume that is not displayed. This volume is imaged in the two portions removed from each input image corresponding to the lengths marked r in FIG. 2. In the case of SCROLL, the missing volume problem is avoided and all portions of each image are shown at one time or another as the image is scrolled.

In order to join images for the reconstruction of a plane, a total of 2 r pixel rows should be removed from the two images. The proportion removed from each image depends upon the position of the scroll. An example is diagrammed in FIG. 5 in which two input images, I and II, are shown on the left. In the case of output image A, the 2 r pixel rows are removed from the top of II. In case B, r pixel rows are removed each from the bottom of I and the top of II. In C, 2 r pixel rows are removed from the bottom of I. In actual scrolling, several output images are constructed and displayed between those shown in FIG. 5, and they have the 2 r pixel rows to be removed proportioned in a continuous fashion.

Inputs to the algorithm are the 5-7 overlapped input images and the skip factor which determines how far the image scrolls from one position to the next. Since the height of the structures of interest changes along the length of the legs, the SCROLL display is improved by finding a new estimate for the number of pixels, r, to remove at each seam.

2.3 Image Enhancement and Equalization

It is sometimes necessary to equalize the brightness of adjoining images in order to make the seam less noticeable. Because the body tapers from thick to thin as one proceeds down the legs, a ramp-type equalization may be used. A general correction image may be constructed that, starting from the top, consists of a flat portion, a ramp portion, and ends with another flat portion. This procedure can be done interactively, or automatically.

In some cases, morphological enhancement of the images is used to decrease the dynamic range of the images and enhance the arteries.

3. Materials and Methods

Images are acquired on a Siemens, Multiskop stepping gantry system using a Polytron for digital image acquisition. Images are acquired using a 40 cm image intensifier which images both legs at once and digitized at 1024×1024 pixels. At each position, new collimation may be set.

All image processing is done in an appropriately programmed computer controller of the Siemens DIGITRON. For the case of SCROLL, many output images are constructed from the input images, and they are displayed using cine replay mode on the DIGITRON. The DIGITRON takes 512×512 pixel images, thus requiring the size of the images to be reduced. A conventional VHS video tape simulate arteries, lead rulers, and lead text strings.

4. Results

WHOLE-LEG gives aesthetically pleasing results and in images with high-arterial contrast often shows more detail that one might expect. SCROLL gives the impression of moving up and down the legs. Physicians have remarked that this is a more intuitive playback method and that it improves the operator's anatomical orientation. Often radiologists show images to referring physicians on the display console. SCROLL should be particularly useful for a quick overview of the patient's condition.

There are several reasons that the planar reconstruction method works well despite the fact that the legs are a three dimensional structure. First, the major structure (bones and arteries) lie vertically in the images with very little structure in the horizontal direction. As described in Results, vertical structures tend to join in continuous lines even when they lie outside the reconstruction plane. Second, at any seam, the structures tend to lie in a single plane. Thus reconstructions are improved by allowing the value of r to change along the length of the leg; that is, new estimates of the best matched pixel rows are obtained for each seam.

Hardware requirements include a fast, general purpose computing element (such as in the DIGITRON) for implementation of the automatic method of finding the best pixel row match. SCROLL requires a large, random access image store (such as in the DIGITRON) for holding all of the input images at once. Display images must be updated fast enough to give a relatively quick scroll.

A problem is that the patient can move within a sequence of frames. This could make it impossible to find a perfect match between adjoining images. This problem is reduced by using the geometric parameters of the acquisition to predict a nominal value and then by restricting the search to ±40 pixels. Thus, a seam will not be far removed from its ideal position. Note that in the case of SCROLL, this is a cosmetic problem only; all pixel rows will still be seen.

Thus, there has been shown and described a novel X-ray examination system using multiple-pass, rapid sweeping of the image acquisition devices, which fulfills all the objects and advantages sought therefor. Many changes, modifications, variations and other uses and applications of the invention will, however, be apparent to those skilled in the art after considering this specification and the accompanying drawings will disclose a preferred embodiment thereof. For example, a possible improvement consists of cutting images along curved lines. Currently, images are cut and joined along straight pixel rows. The images, on the other hand, often have circular tops and bottoms as a result of the round image intensifier. When a circular top or bottom is joined to an adjoining image, there tends to be a gap at the edge of the circular section (see FIG. 8). Pixels exist to fill in this gap and they can be obtained by cutting the images along curved lines instead of the straight pixel rows now used. All such changes, modifications, variations and other uses and applications which do not depart from the spirit and scope of the invention are deemed to be covered by the invention which is limited only by the claims which follow.

I claim:

1. A method for operating an X-ray examination device having an imaging area with a length which is less than the length of an object to be imaged, comprising:

acquiring a series of high-resolution input images at selected different positions which overlap along the length of said object;

processing said series of high-resolution images in accordance with both a first and a second method, said first method determining a low-resolution composite image for providing to said display a composite image which is simultaneously representative of a plurality of said high-resolution acquired images, and said second method determining a portion of each of said high-resolution images which is to be deleted so as to minimize double display of said overlapped length of said object for providing to said display said series of high-resolution images in a sequential fashion; and using the display of the acquired images processed by either one of said first or second methods for controllably indicating a position (region of interest) on said display so as to cause said display to provide a high-resolution image which is centered about said region of interest.

2. A method for operating an X-ray examination device having an imaging area with a length which is less than the length of an object to be imaged, comprising:

acquiring a series of high-resolution input images at selected different positions which overlap along the length of said object;

processing said series of high-resolution images in accordance with both a first and a second method, said first method determining a low-resolution composite image for providing to said display a composite image which is simultaneously representative of a plurality of said high-resolution acquired images, sand said second method determining a portion of each of said high-resolution images which is to be deleted so as to minimize double display of said overlapped length of said object for providing to said display said series of high-resolution images in a sequential fashion; and using the display of the acquired images processed by either one of said first or second methods for controllably indicating a position (region of interest) on said display so as to cause control signals to be applied to a gantry control apparatus for centering said X-ray examination device over said region of interest.

3. Apparatus for operating an X-ray examination device having an imaging area with a length which is less than the length of an object to be imaged, comprising:

means for acquiring a series of high-resolution input images at selected different positions which overlap along the length of said object;

processing said series of high-resolution images in accordance with both a first and a second method, said first method determining a low-resolution composite image for providing to said display a composite image which is simultaneously representative of a plurality of said high-resolution acquired images, and said second method determining a portion of each of said high-resolution images which is to be deleted so as to minimize double display of said overlapped length of said object for providing to said display said series of high-resolution images in a sequential fashion; and means for using the display of the acquired images processed by either one of said first or second methods for controllably indicating a position (region of interest) on said display so as to cause said display to provide a high-resolution image which is centered about said region of interest.

4. Apparatus for operating an X-ray examination device having an imaging area with a length which is less than the length of an object to be imaged, comprising:

means for acquiring a series of high-resolution input images at selected different positions which overlap along the length of said object;

processing said series of high-resolution images in accordance with both a first and a second method, said first method determining a low-resolution composite image for providing to said display a composite image which is simultaneously representative of a plurality of said high-resolution acquired images, and said second method determining a portion of each of said high-resolution images which is to be deleted so as to minimize double display of said overlapped length of said object for providing to said display said series of high-resolution images in a sequential fashion; and means for using the display of the acquired images processed by either one of said first or second methods for controllably indicating a position (region of interest) on said display so as to cause control signals to be applied to a gantry control apparatus for centering said X-ray examination device over said region of interest.

5. The method of claim 1, wherein said second method of said processing step which determines a portion of each of said high-resolution images which is to be deleted, comprises, for adjacent ones of said series of high-resolution images;

searching for correspondingly positioned rows in each of said adjacent images which have at least a predetermined minimum degree of similarity for identifiable features contained therein, said searching beginning near an outer edge of said images and proceeding into said image in a row-by-row manner;

when a pair of correspondingly positioned rows are found having said predetermined minimum degree of similarity, deleting those rows of each of said images which are between said pair of rows and said outer edge of each of said images; and joining a portion of each of said images which remains after said deletion together at said correspondingly positioned rows for subsequent display of said adjacent images as a single displayed image.

6. The method of claim 2, wherein said second method of said processing step which determines a portion of each of said high-resolution images which is to be deleted, comprises, for adjacent ones of said series of high-resolution images:

searching for correspondingly positioned rows in each of said adjacent images which have at least a predetermined minimum degree of similarity for identifiable features contained therein, said searching beginning near an outer edge of said images and proceeding into said image in a row-by-row manner;

when a pair of correspondingly positioned rows are found having said predetermined minimum degree of similarity, deleting those rows of each of said images which are between said pair of rows and said outer edge of each of said images; and joining a portion of each of said images which remains after said deletion together at said correspondingly positioned rows for subsequent display of said adjacent images as a single displayed image.

7. The apparatus of claim 3, wherein said means for processing in accordance with said second method which determines a portion of each of said high-resolution images which is to be deleted, comprises:

means for searching for correspondingly positioned rows in each of adjacent ones of said plurality of images which have at least a predetermined minimum degree of similarity for identifiable features contained therein, and for indicating when a pair of correspondingly positioned rows are found having said predetermined minimum degree of similarity;

means for deleting those rows of each of said images which are between said pair of rows indicated to possess at least said minimum degree of similarity and an outer edge of each of said images; and means for joining that portion of each of said images which remains after said deletion together at said correspondingly positioned rows for subsequent display of said adjacent images as a single displayed image.

8. The apparatus of claim 4, wherein said means for processing in accordance with said second method which determines a portion of each of said high-resolution images which is to be deleted, comprises:

means for searching for correspondingly positioned rows in each of adjacent ones of said plurality of images which have at least a predetermined minimum degree of similarity for identifiable features contained therein, and for indicating when a pair of correspondingly positioned rows are found having said predetermined minimum degree of similarity;

means for deleting those rows of each of said images which are between said pair of rows indicated to possess at least said minimum degree of similarity and an edge of each of said images; and means for joining that portion of each of said images which remains after said deletion together at said correspondingly positioned rows for subsequent display of said adjacent images as a single displayed image.

9. A method for joining together a series of electronically stored images, comprising:

acquiring a plurality of images at selected different positions which overlap each other along a given dimension of an object;

storing each of said acquired images in an electronic memory as a multiple-row array of image pixels;

searching for correspondingly positioned rows in a portion of each of said stored image arrays which have a position overlap therebetween, said searching being for correspondingly positioned rows which have at least a predetermined minimum degree of similarity for identifiable features contained therein and indicating when a pair of correspondingly positioned rows are found having at least said minimum degree of similarity;

deleting those rows of pixels in each of said stored image arrays which are between said indicated pair of rows having at least said minimum degree of similarity and an outer edge of said image array; and joining a portion of each of said image array which remains after said deletion together, said joining being at said correspondingly positioned rows having said at least minimum degree of similarity.

10. An apparatus for joining together a series of electronically stored images, comprising:

means for acquiring a plurality of images at selected different positions which overlap each other along a given dimension of an object;

means for storing each of said acquired images in an electronic memory as a multiple-row array of image pixels;

means for searching for correspondingly positioned rows in a portion of each of said stored image arrays which have a position overlap therebetween, said searching being for correspondingly positioned rows which have at least a predetermined minimum degree of similarity for identifiable features contained therein and indicating when a pair of correspondingly positioned rows are found having at least said minimum degree of similarity;

means for deleting those rows of pixels in each of said stored image arrays which are between said indicated pair of rows having at least said minimum degree of similarity and an outer edge of said image array; and means for joining a portion of each of said image array which remains after said deletion together, said joining being at said correspondingly positioned rows having said at least minimum degree of similarity.

* * * * *